United States Patent [19]

Cullis

[11] Patent Number: 4,636,193
[45] Date of Patent: Jan. 13, 1987

[54] DISPOSABLE CENTRIFUGAL BLOOD PROCESSING SYSTEM

[75] Inventor: Herbert M. Cullis, Silver Spring, Md.

[73] Assignee: Baxter Travenol Laboratories, Inc., Deerfield, Ill.

[21] Appl. No.: 872,822

[22] Filed: Jun. 11, 1986

Related U.S. Application Data

[60] Division of Ser. No. 842,779, Oct. 17, 1977, which is a continuation of Ser. No. 687,290, May 14, 1976, abandoned.

[51] Int. Cl.[4] .............................................. B04B 7/08
[52] U.S. Cl. .................................... 494/45; 215/13 R
[58] Field of Search ....................... 494/45, 21, 43, 85, 494/37, 16, 18, 10, 38, 41; 215/13 R; 210/782, 781, 927

[56] References Cited

U.S. PATENT DOCUMENTS

| | | | |
|---|---|---|---|
| 3,244,363 | 4/1966 | Hein | 494/10 |
| 3,655,123 | 4/1972 | Judson | 494/10 |
| 3,675,846 | 7/1972 | Drucker | 494/45 |
| 3,946,941 | 3/1976 | Weiss | 494/20 |
| 3,955,755 | 5/1976 | Breillatt | 494/10 |
| 3,987,961 | 10/1976 | Sinn | 494/45 |

Primary Examiner—Robert W. Jenkins
Attorney, Agent, or Firm—Paul C. Flattery; George S. Gerstman

[57] ABSTRACT

A continuous flow centrifugal processing system for separating whole blood into fractional components includes a centrifugal separator unit having a molded bowl-shaped outer shell dimensioned to fit within a rotatably-driven casing on an associated centrifuge apparatus. A bowl-shaped inner shell disposed within the outer shell forms therewith a thin separation channel radially spaced from the axis of rotation wherein fractions are separated from the whole blood under the influence of centrifugal force. A rotating seal carried on the processing chamber between ports in the chamber and the non-rotating portions of the system. The outer shell includes a relatively thin side wall portion which is inwardly biased toward a side wall portion on the inner shell when seated in the casing. A plurality of projections on the side walls limit inward deformation of the outer shell to maintain a very close concentric spacing between the shell members to facilitate rapid separation of blood flowing through the chamber. By reason of the shell members being molded, the processing chamber can be economically produced in large quantities for disposable one-time use.

18 Claims, 6 Drawing Figures

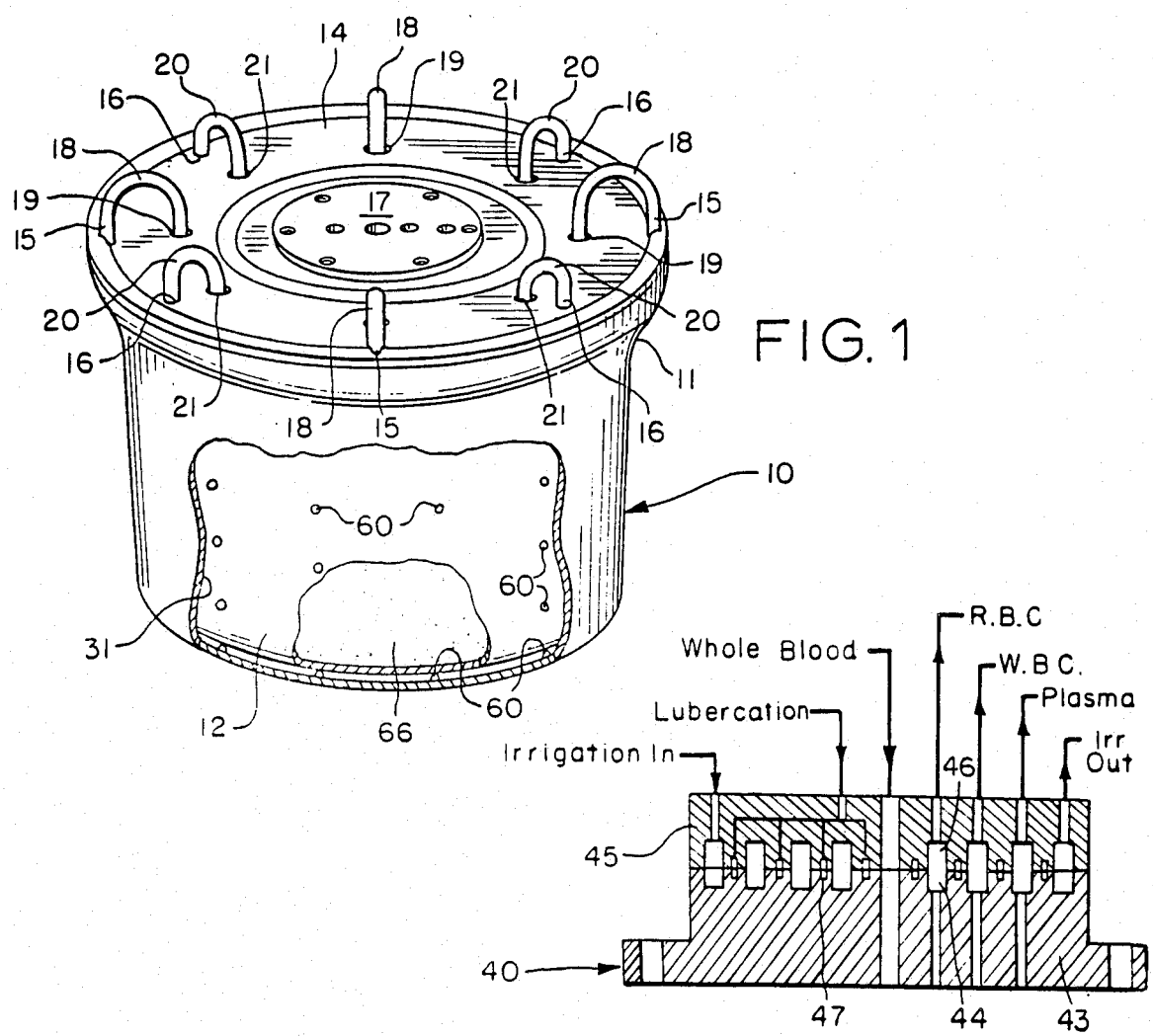
FIG. 1
FIG. 2a
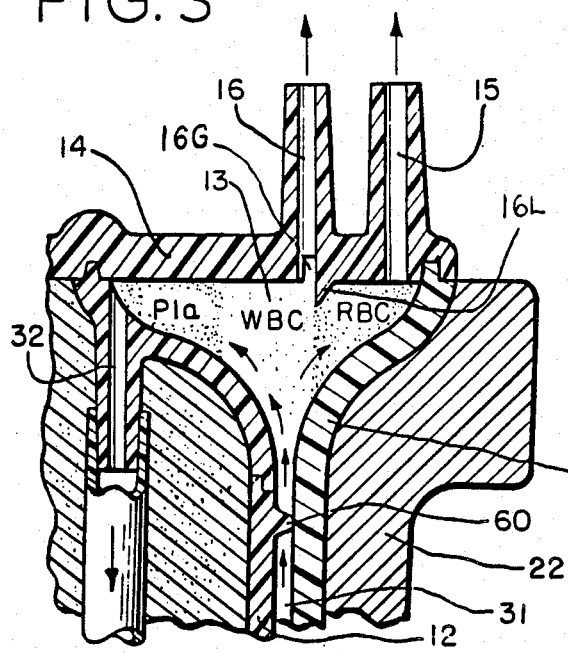
FIG. 3

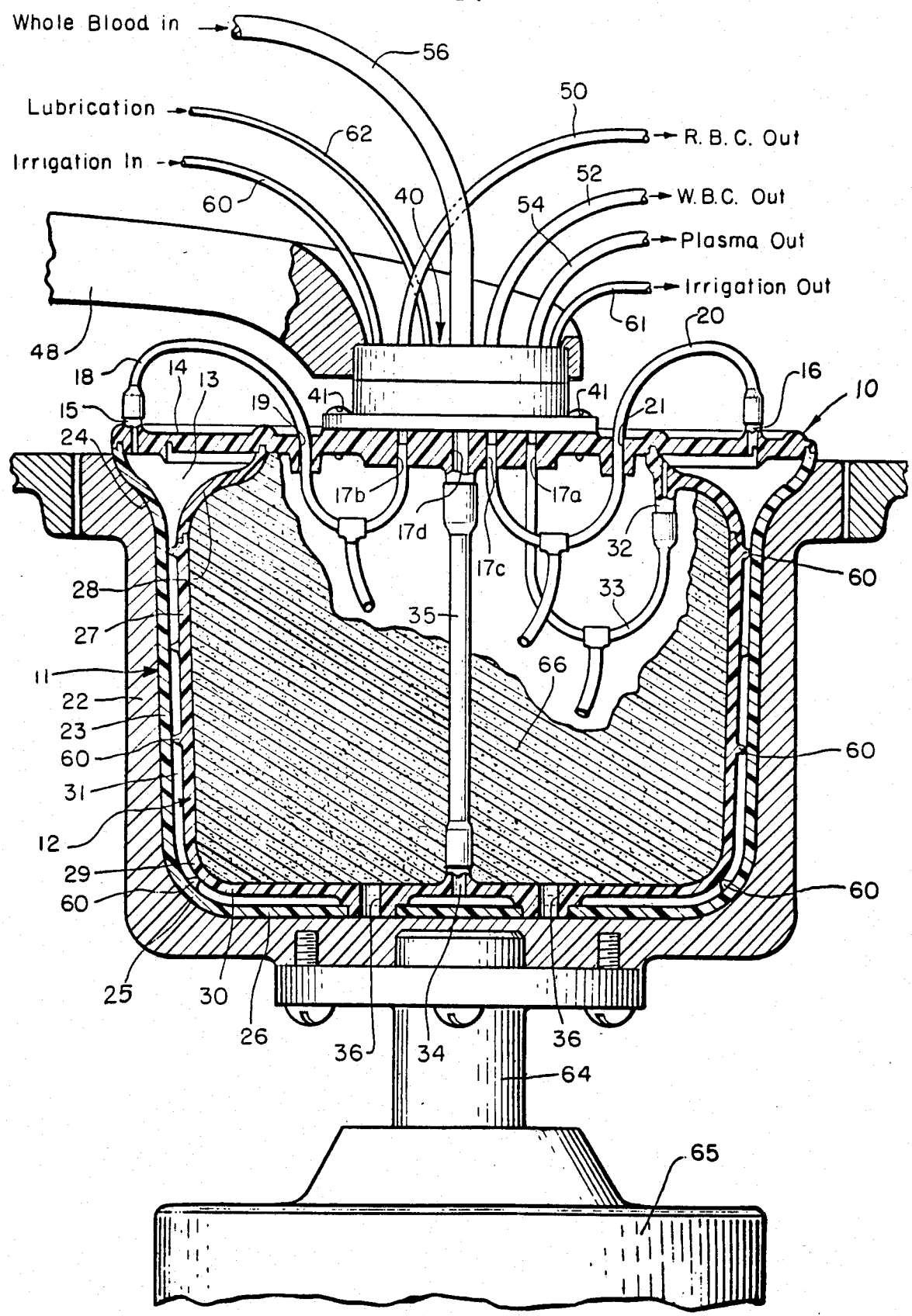

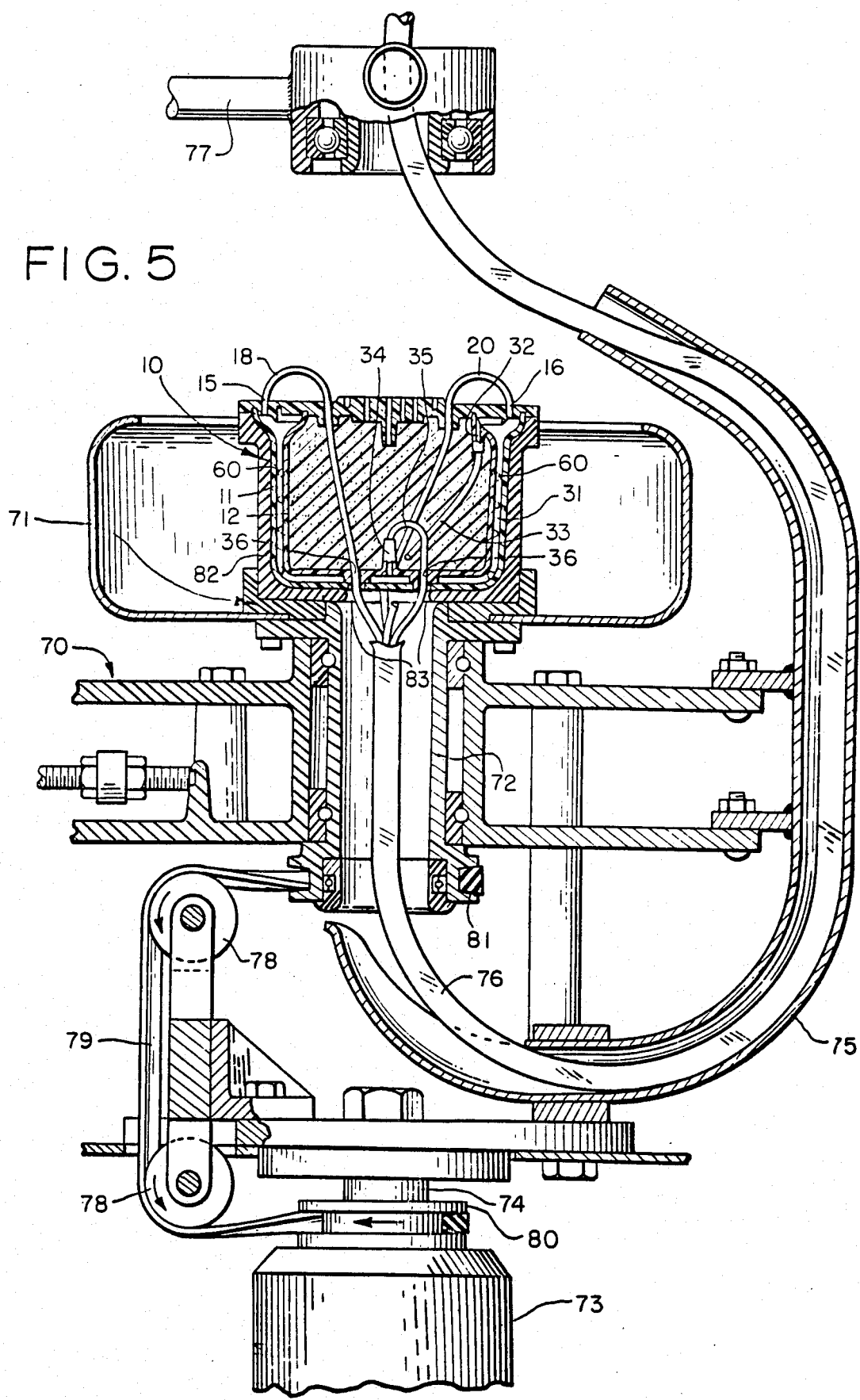

DISPOSABLE CENTRIFUGAL BLOOD PROCESSING SYSTEM

This application is a division of application Ser. No. 842,779, filed Oct. 17, 1977, which is a continuation of application Ser. No. 687,290, filed May 14, 1976, now abandoned.

BACKGROUND OF THE INVENTION

The present invention is directed generally to apparatus for separating or fractionating whole blood into its various individual components, and more particularly to a disposable centrifugal blood separator for use in such apparatus.

Intervivos blood processing apparatus, wherein blood is taken from a live donor, passed through the apparatus, and then returned to the donor, has come into wide use during recent years. During passage through the apparatus, the blood may be separated or fractionated into its component parts, i.e., plasma, red blood cells, and white blood cells or platelets, and some portion of these fractions may be returned to the donor while other portions may be selectively retained within suitable storage means.

Various types of apparatus have been proposed for the intervivos processing of blood. One type of apparatus which has come into wide use is described in U.S. Pat. Nos. 3,489,145 and 3,655,123. This apparatus utilizes a centrifugal separator element in the form of a rotatably driven bowl-shaped outer shell within which a cylindrically shaped center or filler piece is suspended to form a narrow sleeve-shaped separation chamber of very precise dimensions. Fluid connections are established with the chamber by means of a rotating seal, the chamber having an axially-aligned inlet port at one end for admitting whole blood, and a trio of collection ports at the other end for removing red blood cells, white blood cells, and plasma components separated during centrifugation. The structure and operation of a rotating seal for conveying whole blood to the chamber and fractionated blood components from the chamber is described in U.S. Pat. No. 3,519,201.

A major drawback of centrifugal processing units of this type has been their high cost of manufacture. This has resulted primarily because of the very narrow spacing which must be maintained between the inner wall of the outer shell and the outer wall of the central filler in order to achieve efficient separation of the blood components during the very limited transit time in which the blood is actually in the processing chamber. Typically, a spacing of 1.0 to 1.5 mms is necessary for typical transit times of approximately three minutes. This dimension must be maintained with a high degree of concentricity if mixing of the recovered fractions is to be avoided. As a result, the outer shell has heretofore been formed with thick side walls to prevent any variation of the separation channel width during operation of the apparatus.

The need for thick side walls has made it heretofore impractical to mold the inner and outer shells, since the desired thicknesses could not be molded with the necessary precision. Instead, such shells have been extruded and then individually machined, making the cost of manufacture too high for the disposable single-use favored for avoiding contamination.

The present invention is directed to a new and improved construction for the centrifugal processing chamber which enables the unit to be economically fabricated from plastic by known molding techniques while maintaining a processing channel width of 1.5 mm or less with a high degree of concentricity.

SUMMARY OF THE INVENTION

The invention is directed to a disposable continuous flow centrifugal separator for use in conjunction with centrifugation apparatus including a rotatably driven casing for separating fractions from a whole fluid such as blood. The separator includes a molded outer shell dimensioned to be received within the casing in rotatably-locked relation therewith and a molded inner shell disposed within the outer shell in spaced relation thereto. The inner and outer shells include wall portions forming between their inner surfaces a separation chamber radially spaced from the axis of rotation of the casing. The wall portion of the outer shell is relatively thin and flexible whereby the shell is deformed toward the inner shell when seated in the casing. Means in the form of a projection on at least one of the inside surfaces are provided to establish a predetermined spacing between the wall portions, and hence a predetermined width for the separation chamber. Means including an inlet port are provided for supplying whole blood to the separation chamber, and means including a plurality of collection ports communicating with the separation chamber at respective radial distances from the axis of rotation are provided for removing respective separated fractions from the chamber.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view of a centrifugal blood separator constructed in accordance with the invention partially broken away to show the internal construction thereof.

FIG. 2 is an enlarged cross-sectional view of the blood separator installed in a rotating seal type centrifugation apparatus.

FIG. 2a is an enlarged cross-sectional view of the rotating seal assembly utilized in the apparatus shown in FIG. 2.

FIG. 3 is an enlarged cross-sectional view of the downline end of the processing channel illustrating the distribution of fractionated components therein.

FIG. 5 is a cross-sectional view of the centrifugal blood installed within a seal-less centrifugation apparatus.

DESCRIPTION OF THE PREFERRED EMBODIMENT

Figure 4:
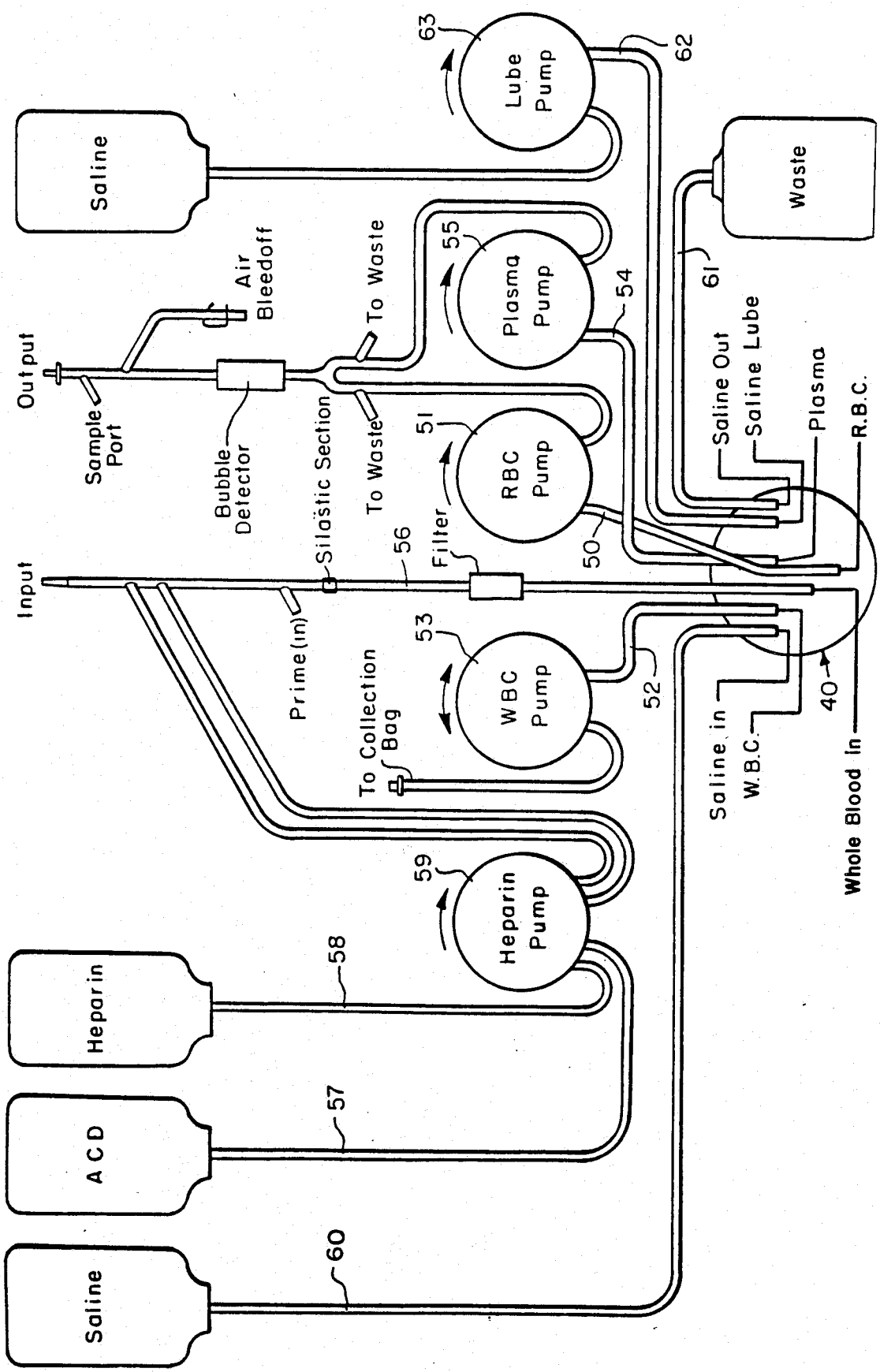
FIG. 4 is a diagrammatic representation of the flow system utilized in conjunction with the centrifugal blood separator of the invention.

Referring to the Figures, and particularly to FIG. 1, a centrifugal blood separator 10 constructed in accordance with the invention includes a bowl-shaped outer shell 11 dimensioned to fit within a similarly shaped recess in a rotatably driven casing (not shown in FIG. 1). A bowl-shaped inner shell 12 is disposed within the outer shell and forms therewith a centrifugal processing chamber 13 within which fractionation of whole blood takes place during rotation of the separator assembly. The rims of the two bowl-shape shells are joined by cemented tongue-and-groove attachments to a flat cover member 14 which includes four red blood cell (RBC) collection ports 15 arranged in a first ring, and four white blood cell (WBC) collection ports 16 arranged at equal intervals in a second ring concentric with the first ring but of lesser diameter. The cover member also includes a plurality of apertures 17 at its center for establishing fluid communication with a rotating seal (not shown in FIG. 1) in a manner to be described presently. Each of the four collection ports 15 is connected to a length of tubing 18 which extends through an aperture 19 in cover member 14 and into the interior of the bowl-shaped inner shell 12. Similarly, each of the collection ports 16 is connected to a length of tubing 20 which extends through an aperture 21 and into the interior of the inner shell member.

Referring to FIG. 2, wherein the centrifugal separator unit is shown in conjunction with a rotating-seal type centrifugation apparatus, the outer shell 11 of the separator is seated in a rotatably driven casing. The outer shell includes a thin upstanding cylindrical side wall portion 23 which terminates at its upward or downline end in an outwardly and then upwardly directed rim portion 24, and at its downward or upline end in an angular portion 25 joining a flat bottom wall portion 26. Similarly, the inside shell 12 includes a thin upstanding cylindrical side wall portion 27, an inwardly and then upwardly directed downline portion 28, and an angular portion 29 joining a flat bottom wall portion 30. The interior surfaces of the side wall portions 23 and 27 together define a separation channel 31 within processing chamber 13 within which RBC, WBC and plasma components are separated from the whole blood as it flows through the channel under the influence of a centrifugal force field. The rim portions 24 and 28 together define a region in chamber 13 of increased width wherein the blood components separated within channel 31 accumulate prior to withdrawal through collection ports 15 and 16.

An additional collection port 32 is provided in the rim portion 28 of inner shell 12 for the purpose of withdrawing plasma as it accumulates in chamber 13. This collection port is connected by a length of tubing 33 to a passageway 17a in top plate 14. Similarly, tubing 18 connects to a passageway 17b and tubing 20 connects to a passageway 17c in top plate 14. To provide means for admitting whole blood into separation channel 31 the inner shell 12 is provided with an inlet port 34 along the axis of rotation of casing 22. This port is connected by a tubing segment 35 to a passageway 17d in cover member 14. Additional apertures 36 may be provided through the bottom wall portions 26 and 30 of the inner and outer shells to facilitate installation of the separator 10 in a seal-less type centrifugal apparatus in a manner to be described presently.

To provide fluid communication between the inlet and collection ports and the non-rotating portions of the flow system associated with the separator a rotating seal assembly 40 is provided on top plate 14 along the axis of rotation of casing 22. This seal assembly, which may be conventional in construction and operation, is mounted to top plate 14 by means of suitable fastening devices such as bolts 41. Referring to FIG. 2a, the rotating seal assembly consists of a rotating member 43 having a plurality of ring-shaped recesses 44 therein and a stationary member 45 having a plurality of communicating ring-shaped recesses 46 therein. Individual lands 47 are provided between respective ones of the recesses to maintain fluid isolation and additional irrigation and/or lubrication flow systems may be provided for improved operation in a manner well known to the art.

In practice, two passageways are provided in top plate 14 for each ring-shaped recess associated with a fractional component, and each of these passageways may in turn be connected by an appropriate Y-connector and appropriate lengths of connecting tubing to respective ones of the four collection ports associated with that fraction. These connections have not been shown in FIG. 2 for the sake of clarity.

The upper non-rotating portion 45 of the rotating seal assembly 40 is held in a stationary non-rotating position in compression-engagement with the lower rotating portion 43 by means of a retaining arm 48 mounted on the frame of the centrifugation apparatus. The lower rotating portion of the seal may consist of a polished ceramic disc attached to member 14 by means of concentric silastic O-rings which establish fluid communication between recesses 44 and appropriate ones of passageways 17. The upper stationary portion of the seal is formed of stainless steel lapped to insure perfect contact with the ceramic disc. Each of the ring-shaped recesses 46 thereon is connected by a passageway to a tubing port on the top of the disc.

Referring to FIG. 4, the RBC outlet port is connected by a tubing segment 50 to a peristaltic pump 51, the WBC outlet port is connected by a tubing segment 52 to a peristaltic pump 53, and the plasma outlet port is connected by a tubing segment 54 to a peristaltic pump 55. Whole blood is supplied to the inlet port by a tubing segment 56, to which acid citrate dextrose (ACD) and Heparin are introduced through respective tubing segments 57 and 58 and a peristaltic pump 59. Saline is supplied to the rotating seal for isolation purposes through a tubing segment 60 and exhausted through a tubing segment 61. Saline is supplied to the seal for lubrication purposes by means of a tubing segment 62 and a peristaltic pump 63.

The white blood cells, red blood cells and plasma derived by the system may be pumped to respective collection bags for storage or may be returned to the donor as required. Various safety devices may be incorporated into the system to guard against leakage of air or undue temperature rise, or the occlusion of a vein in the donor.

Casing 22 is mounted on a drive shaft 64 which in turn is rotatably driven by means of a motor 65. In practice, this drive arrangement is designed and constructed to provide a very high degree of concentricity in the rotation of casing 22 to insure efficient operation of the separation process and efficient operation of the seal assembly 40.

In operation, casing 22 is rotated at approximately 800 rpm to establish a centrifugal force field across separation channel 31. The flow path is next primed with sterile saline solution and all air bubbles are removed by back-flushing the system through the WBC peristaltic pump 53. Whole blood is then admitted through tubing 56, rotating seal assembly 40, and tubing segment 35 to inlet port 34. The whole blood flows radially outwardly within chamber 13 and upwardly through separation channel 31. The centrifuge speed is now adjusted to achieve separation of the RCB, WBC and plasma components in the manner illustrated in FIG. 3. Separation begins as the blood flows up the side of the bowl toward the collection ports, the blood eventually separating into three concentric bands, with the dense red blood cells outermost, and the less-dense white blood cells, or buffy coat, at an intermediate radius and the least-dense plasma at the shortest radius. Platelets are generally distributed among all three regions, but can be concentrated somewhat by varying the centrifuge speed. Collection ports 15, 16 and 32 remove the components from processing chamber 13 for collection or return to the donor as desired.

Typically, the flow rate of the whole blood in chamber 13 is such that the residence time of the blood in the chamber is about three minutes. To insure that separation of the blood components will take place within this relatively short period of time it is necessary that the width of the separation channel 31 be very small, typically in the order of 1.5 mm or less. To obtain efficient separation of the blood components this dimension must be maintained with a high degree of concentricity so that the components as they separate will flow upwardly to the collection area at the upper end of chamber 13.

To insure that the desired separation channel width is maintained with the desired degree of concentricity, the outer and/or inner shell members are provided, in accordance with the invention, with a plurality of inwardly-projecting integrally-molded spacing bosses 60 which bear against their opposing shell surface to maintain accurate spacing. To insure that these bosses will in fact be determinative of the inter-element spacing, the outer shell 11 is dimensioned such that when the separator unit 10 is seated in casing 22 the side walls of the outer shell are caused to deform inwardly to a slight extent. This deformation is sufficient to bring the spacing bosses 60 into engagement with their opposing wall surfaces and assure that the desired spacing is established and maintained. To facilitate insertion of the separator unit in casing 22 the outer shell is preferably formed with a slight inward taper, typically in the order of one degree, and the inner wall of casing 22 is formed with a complimentarily taper.

The inner and outer shells are preferably molded of a polycarbonate plastic such as Lexan (a trademark of General Plastic Corporation) by means of conventional molding techniques. The sidewalls 23 and 27 of these shells may have a thickness of 0.125 inch to obtain the desired inward deformation when the separator is seated in casing 22. In a representative application, the separator 10 is formed with an outside diameter of approximately 6 inches and a height of approximately 4 inches. With a processing channel 31 1.5 mm wide, the processing chamber 13 has a volume of approximately 140 ml.

Once the various lengths of tubing have been installed during manufacture of the separator unit 10 the volume enclosed within the inner shell 12 may be filled with a foam material 66 to prevent accumulation of significant quantities of fluid within the chamber. This is a safety feature to insure that any leakage will be immediately evident to the operator and will not accumulate within the rotating bowl assembly.

Referring to FIG. 5, the centrifugal separator unit of the invention may also be utilized in conjunction with a seal-less centrifugation apparatus such as that described and claimed in the co-pending application of Houshang Lolachi, Ser. No. 657,187, filed Feb. 11, 1976 now U.S. Pat. No. 4,113,173, and assigned to the present assignee. Basically, this centrifugation apparatus includes a rotor drive assembly 70 to which a rotor assembly 71 is journaled by means of a hollow support shaft 72. The rotor drive assembly 70 is journaled to a stationary hub assembly 73 by means of a vertical drive shaft 74, and includes a guide sleeve 75.

The centrifugal processing chamber 10 of the invention is seated on the rotor assembly 71. Fluid communication is established between the separator unit, which rotates with the rotor assembly 71, and the non-rotating portion of the flow system, which may be identical to that shown in FIG. 4 except for the omission of the rotating seal member 40, by means of a four channel umbilical cable 76 which extends from a central location along the axis of rotation of the separator unit downwardly through the center of drive shaft 72, radially outwardly through guide sleeve 75 and upwardly to a fixed axially-aligned position established by a support arm 77. As described in the previously identified co-pending application Ser. No. 657,187, this routing of the umbilical cable 76, together with the rotor assembly 71 and rotor drive assembly 70 being driven in the same direction with a speed ratio of 2:1, establishes fluid communication with centrifugal separator unit 10 without the cable becoming twisted. Instead, the umbilical cable is subjected only to flexing, or repeated partial twists about its axis through angles not in excess of 180 degrees, as the rotor assembly 71 rotates.

To obtain the desired 2:1 speed ratio between the rotor and rotor drive assembly two pairs of idler pulleys 78 are mounted on rotor drive assembly 70. A drive belt 79 is routed over these pulleys and around a stationary ring-type pulley 80 mounted on hub 73 at one end, and around a rotor drive pulley 81 carried on the bottom end of the rotor drive shaft 72 at its other end. As the rotor drive assembly 70 is rotated clockwise by means of a motor (not shown) driving drive shaft 74, drive belt 79 establishes a clockwise rotation of rotor assembly 71. Assuming that stationary pulley 80 and rotor drive pulley 81 have the same diameter, the rotational speed of rotor assembly 71 will be exactly twice that of rotor drive assembly 70, by reason of the combined effect of the direct 1:1 drive relationship established by pulleys 80 and 81 and the planetary motion of idler pulleys 78 about the rotational axis of rotor assembly 71.

In order that the centrifugal separator unit 10 can be seated in rotor assembly 71 the tubing segments 18, 20 and 33 associated with collection ports 15, 16 and 32 are routed through the center of the separator unit and down through apertures 36 in the bottom walls of the inner and outer shell members. A casing 82, which may be similar to casing 22 in all respects except for the provision of passageways 83 in its bottom wall for accommodating the connecting conduit segments, is mounted on rotor assembly 71 to receive the centrifugal separator unit. As with the previously described rotating seal embodiment, the wall of the outer shell is compressed by casing 82 to obtain a separation channel 31 having a high degree of concentricity. The individual connecting tubing segments after passing through passageways 83 are joined into umbilical cable 76.

It is contemplated that the centrifugal separator unit 10 when intended for use in a seal-less centrifugation apparatus such as that shown in FIG. 5 would be manufactured as a single integral disposable unit in which umbilical cable 76 is included. To install this unit in the apparatus the free end of the umbilical cable could be threaded downwardly through the hollow rotor support shaft 72 and then radially outwardly and upwardly through sleeve 75 to support arm 77. The free end of the cable would then be pulled through until the separator unit was seated in casing 82. After use, the entire assembly would be removed from the apparatus and disposed of.

A centrifugal blood separator unit has been shown and described which provides efficient processing of blood into its constituent components. The separator unit can be economically formed by known molding techniques, and by reason of its low cost of manufacture, is ideally suited for disposable one-time use situations wherein the dangers of contamination to the donor from prior uses are completely avoided.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

As is best shown in FIG. 3, a concentric lip 16L is provided having an inner surface aligned with the outer side of the white blood cell collection ports 16, and the adjacent bottom surface of the cover member 14 is provided with a concentric groove 16G into which the ports 16 open. The provision of this groove and lip has resulted in experimentally verified better separation of the red blood cells from the collected white blood cells.

It has been found in the bowl that only four spacer units 60 need to be employed and that the spacer flange between the inner and outer shells at 36 serves to not only fix the horizontal wall (bottom to top) spacing but also, to a significant degree, to fix the side wall spacing. In one embodiment only four spacers 60 were used successfully. These were positioned near the upper surface at equal spacing around the unit. One experimental bowl which was constructed in accordance with the present invention was made of polycarbonate molded in four parts and had an overall height of approximately four inches and a diameter of approximately six and one-eighth inches. This particular unit has a fluid capacity of only 143 ml which compares favorably with the prior art bowls of this type.

The shells 11 and 12 were of approximately ⅛ inch thickness and maintained a spacing of 0.050 inches. The outer shell, although reasonably rigid for handling purposes, was slightly out-of-round and under the increased forces of centrifugation might have deformed even more. However, with a true round casing 22, and of stainless steel, the outer shell was upon insertion caused to go into a true round and concentric shape.

It should be noted that the four molded ports of the bowl 10 of the two embodiment (FIGS. 1-2 and FIG. 5) are identical and may be adaptable to either configuration. The present invention allows for these ports to be manufactured with greater dimensional tolerances than is the case with prior art permanent type bowls and yet achieve good results.

It is contemplated that the disposable bowls of the present invention of the FIGS. 1-2 type could be easily retrofitted to existing commercial machines such as the CELLTRIFUGE ® separator unit made by the American Instrument Company division of Travenol Laboratories, Inc., by the securing of an appropriate casing in the unit. Of course, similar casings could be used to enable other brands of such machines to be similarly retrofitted.

Although polycarbonate is the plastic presently preferred in making the outer shell and other of the blood contacting ports, other plastic materials may also be used, such as methyl methacrylate, styrene-acrylonitrile, acrylic, styrene, or acrylonitrile. While molding is the presently preferred method of manufacture, it is also possible to form the shells by vacuum forming or casting.

Also, although the inner shell is depicted as hollow and later preferably filled with form, the term "inner shell" should be understood in the claims to include solid units.

I claim:

1. A disposable continuous flow centrifugal separator for use in conjunction with centrifugation apparatus including a rotatably driven casing for separating fractions from a whole fluid, said separator comprising, in combination:

a molded outer shell received within said casing in rotatably-locked relation therewith;

a molded inner shell disposed within said outer shell in spaced relation thereto, said inner and outer shells including wall portions forming between their inner surfaces a separation chamber radially spaced from the axis of rotation of the casing, the wall portion of said outer shell being relatively thin and deformable and resiliently biased toward said inner shell when seated in said casing;

means including a plurality of projections on at least one of said inner surfaces in abutting engagement with the other of said inner surfaces for establishing a predetermined concentricity between said wall portions;

inlet means including an inlet port for supplying whole blood to be processed to said separation chamber; and outlet means including a plurality of collection ports communicating with said separation chamber at respective radial distances from said axis of rotation for removing respective separated fractions from said chamber.

2. A disposable centrifugal separator as defined in claim 1 wherein said inner and outer shells are bowl-shaped and said casing forms a bowl-shaped recess for receiving said outer shell.

3. A disposable centrifugal separator as defined in claim 2 wherein said inlet port is coaxial with the axis of rotation of the separator.

4. A disposable centrifugal separator as defined in claim 2 wherein said inner and outer shells include rim portions, and wherein a substantially flat cover member is secured to said rim portions.

5. A disposable centrifugal separator as defined in claim 4 wherein at least a portion of said collection ports are in said top cover.

6. A disposable centrifugal separator as defined in claim 4 wherein said inner shell includes at its upper end an inwardly and upwardly directed rim portion, and wherein said outer shell includes at its upper end an outwardly and upwardly directed rim portion, said rim portions forming therebetween a separator chamber of increased radial width.

7. A disposable centrifugal separator as defined in claim 2 wherein said outer shells are made of relatively thin plastic material.

8. A disposable centrifugal separator as defined in claim 2 wherein said inner and outer shells are molded of a thin plastic polycarbonate material.

9. A disposable centrifugal separator as defined in claim 4 wherein said cover member includes at least one passageway for establishing fluid communication with said collection ports.

10. A disposable centrifugal separator as defined in claim 1 wherein said outlet means include first, second and third collection ports disposed at respective first, second and third radial spacings from said axis of rotation.

11. A disposable centrifugal separator as defined in claim 10 wherein said whole fluid comprises whole blood, and said first, second and third fractions comprise red blood cells, white blood cells and plasma, respectively.

12. A disposable centrifugal separator as defined in claim 1 wherein said projections comprise a plurality of inwardly-extending bosses on said inside surfaces of said shells.

13. A disposable centrifugal separator as defined in claim 1 wherein said projections comprise a plurality of inwardly-extending bosses on said inside surface of said one shell.

14. A disposable centrifugal separator as defined in claim 13 wherein said outlet means include first, second and third collection ports disposed at respective first, second and third radial spacings from said axis of rotation.

15. A disposable centrifugal separator as defined in claim 14 wherein said fractions comprise red blood cells, white blood cells and plasma.

16. A disposable centrifugal separator as defined in claim 13 wherein said means for establishing a predetermined spacing comprise a plurality of inwardly-extending bosses on said inside surfaces of said shells.

17. A disposable continuous-flow centrifugal blood separator for use in conjunction with centrifugation apparatus including a rotatably-driven bowl-shaped casing for separating RBC, WBC and plasma fractions from whole blood, said separator comprising, in combination:
 a molded outer bowl-shaped shell received within said casing in rotatably-coupled relationship thereto;
 a molded bowl-shaped inner shell disposed within said outer shell in spaced relationship thereto, said inner and outer shells including generally cylindrical upstanding wall portions forming therebetween a thin sleeve-shaped separation chamber radially-spaced from the axis of rotation of the casing, the wall portion of said outer shell being relatively thin and deformable whereby said shell is deformed toward the wall of said inner shell when seated in the casing;
 means including a plurality of projections on the inside surface of at least one of said wall members in abutting engagement with the inside surface of the other of said wall members for establishing a predetermined concentricity between said wall portions;
 inlet means including an inlet port for supplying whole blood to be processed to said separation chamber; and
 outlet means including a plurality of collection ports communicating with said separation chamber at respective radial spacings from said axis of rotation to remove respective ones of the separated blood fractions from said chamber.

18. A system for continuous centrifugal processing of whole blood into separated fractions comprising, in combination:
 centrifugation apparatus including a rotatably driven casing having a bowl-shaped recess therein;
 a molded outer shell seated within said recess, and rotatably coupled thereto;
 a molded inner shell disposed within said outer shell in spaced relationship thereto;
 said inner and outer shells including wall portions forming therebetween a separation chamber radially spaced from the axis of rotation of the casing, said wall portion of said outer shell being relatively thin and deformable and inwardly biased by said casing;
 spacing means including projections on the inside surface of at least one of said wall portions in abutting engagement with the inside surface of the other of said wall portions for establishing a predetermined concentricity between said wall portions;
 inlet means including an inlet port for supplying whole blood to be processed to said separation chamber;
 outlet means including a plurality of collection ports communicating with said separation chamber at respective radial spacings from said axis of rotation to remove respective separated blood fractions from said chamber; and
 fluid transfer means for conveying fractions of said whole blood developed at said collection ports to respective storage or utilization means.

* * * * *